United States Patent [19]

White

[11] 4,012,408

[45] Mar. 15, 1977

[54] LUBRICATING OIL ADDITIVES

[75] Inventor: James A. White, Houston, Tex.

[73] Assignee: Texaco Inc., New York, N.Y.

[22] Filed: Dec. 19, 1974

[21] Appl. No.: 534,390

Related U.S. Application Data

[62] Division of Ser. No. 486,148, July 5, 1974, Pat. No. 3,896,050.

[52] U.S. Cl. .......................................... 260/302 A
[51] Int. Cl.$^2$ .................................... C07D 375/02
[58] Field of Search .................... 260/302 A, 302 S Primary Examiner—Donald G. Daus
Assistant Examiner—D. B. Springer
Attorney, Agent, or Firm—T. H. Whaley; C. G. Ries; Kenneth R. Priem

[57] ABSTRACT

Lubricating oils of superior copper corrosion inhibiting properties may be made using an additive of 3,5-bis(alkyldithio)-4-substituted isothiazoles as additives.

2 Claims, No Drawings

LUBRICATING OIL ADDITIVES

This is a division of application Ser. No. 486,148, filed July 5, 1974, now U.S. Pat. No. 3,896,050, issued July 22, 1975.

BACKGROUND OF THE INVENTION

1. Field of the Invention

This invention relates to the field of lubricating oil additives, particularly copper corrosion inhibitors.

2. Description of the Prior Art

Various lubricating oils including gear oil, turbine oil, and hydraulic oil, to name a few, may be corrosive to copper due to certain additives which they often contain. Therefore, in lubricating oil wherein copper corrosion is a problem a copper corrosion inhibitor will eliminate the problem. A commercially available copper corrosion inhibitor is dialkyl-2,5-bis (octyldithio)-1,3,4-thiadiazole. I have discovered a different and new corrosion inhibitor which exhibits better performance.

SUMMARY OF THE INVENTION

My invention is a lubricating oil comprising a major amount of a base oil and a minor amount of a copper corrosion inhibitor of the general formula:

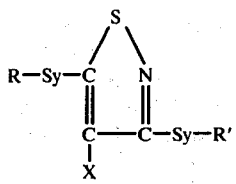

Wherein:
R and R′ = $C_1$ to $C_{20}$ alkyl and may be the same or different
Y = 2 or more
X = CN or COOR″ or R‴ wherein R″ is alkyl substituted with oxygen or sulfur and R‴ is $C_1$ to $C_{20}$ alkyl or cycloalkyl which may be described as a 3,5-bis(alkyldithio)-4-substituted isothiazole. My invention is also the compositions comprising the copper corrosion inhibitors of my invention.

DESCRIPTION OF THE PREFERRED EMBODIMENTS

The copper corrosion inhibitors of my invention are substituted isothiazoles of the following general structure:

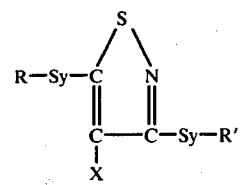

Wherein:
R and R′ = $C_1$ to $C_{20}$ alkyl and may be the same or different
Y = 2 or more
X = CN or COOR″ or R‴ is alkyl or alkyl substituted with oxygen or sulfur and R‴ is $C_1$ to $C_{20}$ alkyl or cycloalkyl More specifically substituted isothiazoles of my invention may be represented by the following formula:

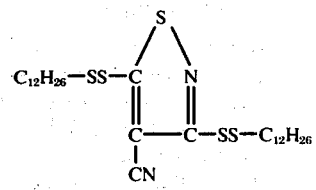

Wherein:
R and R′ = $C_6$ to $C_{13}$ alkyl and may be the same or different
Y = 2 to 4
X = CN or COOR″ or R‴ wherein R″ is alkyl or alkyl substituted with oxygen or sulfur and R‴ is $C_1$ to $C_{20}$ alkyl or cycloalkyl A particularly preferred substituted isothiazole of my invention is:

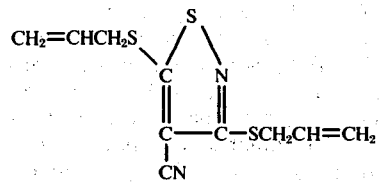

These compounds are in sharp contrast to isothiazoles as disclosed in U.S. Pat. No. 3,230,229 (Example 21) which have the following general structure:

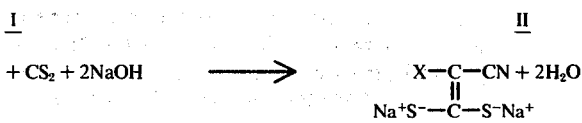

Compounds of the patent are thioethers whereas the compounds of my invention contain at least a disulfide linkage which imparts completely different chemical properties to the compounds of my invention.

Synthesis of 3,5-bis(alkyldithio)-4-substituted isothiazoles

A non-limiting synthesis scheme for the compounds of my invention may be depicted as follows:

$$\underset{I}{X-CH_2-CN + CS_2 + 2NaOH} \longrightarrow \underset{II}{\underset{Na^+S^--C-S^-Na^+}{X-\overset{\|}{C}-CN + 2H_2O}}$$

(X = CN, COOR" or R'" wherein R" is alkyl or alkyl substituted with oxygen and R'" is $C_1$ to $C_{20}$ alkyl or cycloalkyl)

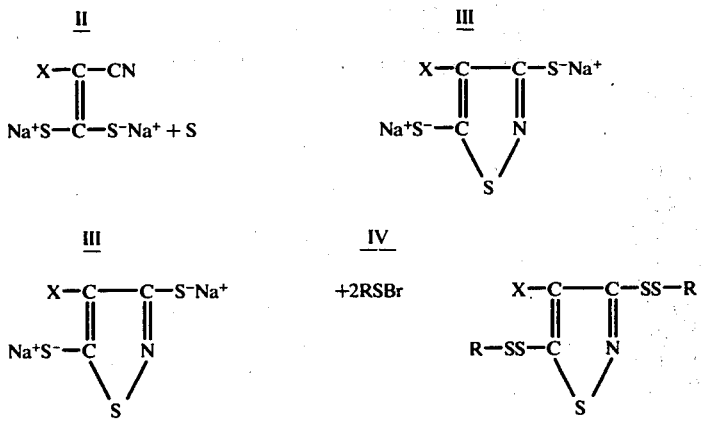

(R = $C_1$ to $C_{20}$ alkyl)

Synthesis Procedure

A synthesis was carried out as follows:

A reaction flask was charged with 900 ml of methanol and 880 grams (2.0 moles) of sodium hydroxide and the mixture was cooled to 50° F by use of an external cooling bath. A malonitrile solution, 66 grams (1.0 moles) and 50 ml of methanol, was added drop-wise to the cooled solution keeping the temperature between 25° and 70° F, preferably 50° F. As soon as the malonitrile solution had been added 60.3 ml (1.0 mole) of carbon disulfide was added over a 30 minute period, keeping the temperature between 25° and 70° F, preferably 50° F. The resulting heavy, yellow slurry was stirred for one hour maintaining a temperature between 50° – 60° F, then the temperature was allowed to rise to room temperature. Sulfur, 32 grams (1.0 mole) was added at room temperature and the solution was refluxed for 30 minutes then filtered to remove any unreacted sulfur. The 3,5-di-(sodiomercapto)-4-isothiazole carbonitrile (III) was retained as a methanol solution to be reacted with the chosen alkyl sulfonyl bromide.

Dodecyl sulfony bromide (IV) was prepared by adding dodecyl mercaptan, 80.8 grams (0.40 mole) drop-wise to a solution of 64 grams (0.40 mole) of bromine in 300 ml of carbon tetrachloride. During the reaction the temperature was maintained between 25° and 70° F, preferably about 50° F. After the dodecylmercaptan was added, the mixture was nitrogen blown for 2 hours to remove traces of hydrobromic acid. The dodecyl sulfenyl bromide (IV) was held in the cold box at 40° F.

Part of the solution of 3,5-bis(sodiomercapto)-4-isothiazole, preparation given above, about 200 ml, (0.2 mole active component) was placed in a reaction flask and cooled to 60° F. The cold solution of dodecysulfenyl bromide was added as rapidly as possible keeping the temperatures between 30° and 60° F, preferably about 50° F. The mixture was stirred an additional 30 minutes keeping the temperature near 50° F. The layers were separated and a carbon tetrachloride layer was washed two times with 100 ml of distilled water each time. The organic layer was dried, filtered and evaporated to constant weight at 175° F to yield 58.5 grams of 3,5-bis(dodecyldithio)-4-cyanoisothiazole, the product of my invention (V). Analysis were: %C-63.9, %H-4.3, %N-4.3, %S-26.5.

Use of the Copper Corrosion Inhibitor

The type of compound synthesized above is suitable for use in automotive lubricating oils, gear oils, turbine oils, and hydraulic oils, circulating oils and other industrial lubricants. It is thermally and hydrolytically stable and does not degrade water separation properties. High concentrations of inhibitor are not corrosive to copper and possess mild EP characteristics. The suggested concentration range in a lubricant is from 0.001 to 5.00 weight percent, but the preferred range is from 0.01 to 0.50 weight percent depending on the application. The substituent on compound I in the synthesis scheme above, can be CN, COOR" where R" is $C_1$ to $C_{20}$ alkyl or alkyl substituted with oxygen or sulfur, and R'" is $C_1$ to $C_{20}$ alkyl but is preferably $C_6$ to $C_{13}$ alkyl to lend oil solubility to the compound.

Oil blends containing ditertiarynonylpolysulfides, compounds corrosive to copper, were used to evaluate the activity to the subject compound compared to a commercial inhibitor. The results presented in the attached Table I indicate that the isothiazole inhibitor of my invention (Prepared as in "Synthesis Procedure" above) gave improved copper corrosion inhibition compared to the commercial inhibitor.

In the following Table I, a Turbine Oil base oil was tested for copper corrosion using additives as indicated. The measurement of copper corrosion was according to ASTM D-130. The copper corrosion grows more severe as the number increases. The tests indicate overall better performance using the corrosion inhibitor of my invention as compared to the commercially available product.

Table I

| Additive DNPS* | Wt. % Invention Inhibitor** | Commercial Inhibitor A*** | Copper Strip Corrosion 3 hrs/212° F |
|---|---|---|---|
| 0.5 | — | — | 4a |
| 0.5 | 0.05 | — | 2a |
| 0.5 | 0.10 | — | 1b |
| 0.5 | — | 0.05 | 2a |
| 0.5 | — | 0.10 | 3b |
| — | 2.00 | — | 1a |

*DNPS - ditertiarynonyl polysulfide
**3,5-bis(dodecyldithio)-4-cyanoisothiazole
***2,5-bis(t-octyldithio)-1,3,4-thiadiazole A nonlead gear oil formulation meeting U.S. Steel Spec. 224 was used to compare the effectiveness of my isothiazole inhibitor with two commercial inhibitors in the severe 3hr/250° F Copper Strip Corrosion Test. The results presented in Table II indicate that the isothiazole inhibitor was completely equivalent to both Commercial Inhibitors A and B in the industrial gear oil formulation. This demonstrates further the effectiveness of the corrosion inhibitor of my invention.

Table II

| Invention Inhibitor | Commercial Inhibitor A | Commercial Inhibitor B[1] | Copper Strip Corrosion[2], 3hrs/ 250° F |
|---|---|---|---|
| — | — | — | 2c, 2c |
| 0.05 | — | — | 1b, 1b |
| — | 0.05 | — | 1b, 1b |
| — | — | 0.05 | 1b, 1b |

[1]2,5-bis(n-octyldithio)-1,3,4-thiadiazole
[2]U.S. Steel Spec. 224 quality gear oil was used as the base blend.

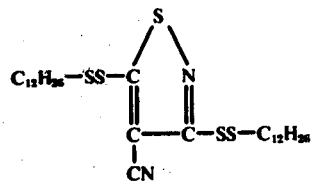

I claim:
1. A compound of the formula

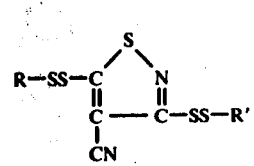

wherein:
R and R' = $C_1$ to $C_{20}$ alkyl and may be the same or different.

2. The compound